(12) United States Patent
Glattstein et al.

(10) Patent No.: US 10,260,999 B2
(45) Date of Patent: Apr. 16, 2019

(54) SAMPLING DEVICE

(71) Applicants: Amichai Glattstein, Jerusalem (IL);
Baruch Glattstein, Jerusalem (IL)

(72) Inventors: Amichai Glattstein, Jerusalem (IL);
Baruch Glattstein, Jerusalem (IL)

( * ) Notice: Subject to any disclaimer, the term of this patent is extended or adjusted under 35 U.S.C. 154(b) by 330 days.

(21) Appl. No.: 14/429,377

(22) PCT Filed: Sep. 19, 2013

(86) PCT No.: PCT/IB2013/002051
§ 371 (c)(1),
(2) Date: Mar. 19, 2015

(87) PCT Pub. No.: WO2014/045099
PCT Pub. Date: Mar. 27, 2014

(65) Prior Publication Data
US 2015/0233795 A1      Aug. 20, 2015

Related U.S. Application Data

(60) Provisional application No. 61/703,049, filed on Sep. 19, 2012.

(51) Int. Cl.
*G01N 1/22* (2006.01)
*G01N 1/24* (2006.01)
(Continued)

(52) U.S. Cl.
CPC ............ *G01N 1/22* (2013.01); *G01N 1/2202* (2013.01); *G01N 1/24* (2013.01); *G01N 21/78* (2013.01);
(Continued)

(58) Field of Classification Search
USPC .......................... 73/863.3; 422/56, 86; 436/8
See application file for complete search history.

(56) References Cited

U.S. PATENT DOCUMENTS 5,679,535 A * 10/1997 Joyce ................... G01N 1/2205
15/246.2
5,981,287 A * 11/1999 Sinclair .............. G01N 33/6839
436/164
(Continued)

FOREIGN PATENT DOCUMENTS

GB         2341117    *  3/2000   ............... G01N 1/24
WO   WO-2004081541 A1 *  9/2004   ............. B01L 3/502
(Continued)

*Primary Examiner* — Nina Bhat

(57) ABSTRACT

Particle collecting unit for the detection of particles in the particle level of substance without evaporating the collected particles is disclosed. The particle collecting unit comprises a body, a duct extending through the body and connecting between a rear opening of the body and an air intake orifice of the body, an aperture or slit in a mid-portion of the body adapted for receiving a removable sampling member into a position within the duct, wherein the particles collecting unit is configured to be removably coupled to a vacuum generator of a vacuum cleaner model available in the market, with said rear opening of the body coupled to an air intake opening of the vacuum generator. Pressure release openings are provided in walls of the duct for reducing the load on a motor of the vacuum cleaner.

18 Claims, 2 Drawing Sheets

(51) Int. Cl.
    *G01N 21/78*     (2006.01)
    *G01N 33/00*     (2006.01)
    *G01N 33/15*     (2006.01)
    *G01N 15/06*     (2006.01)
    *G01N 1/02*     (2006.01)

(52) U.S. Cl.
    CPC ......... *G01N 33/0057* (2013.01); *G01N 33/15* (2013.01); *G01N 15/0606* (2013.01); *G01N 2001/022* (2013.01); *G01N 2033/0091* (2013.01); *G01N 2201/02* (2013.01)

(56) References Cited

U.S. PATENT DOCUMENTS

| 7,122,065 | B2* | 10/2006 | Fox | G01N 1/24 55/306 |
|---|---|---|---|---|
| 7,410,612 | B1 | 8/2008 | Carrington | |
| 7,574,930 | B2 | 8/2009 | Bunker | |
| 7,575,717 | B2* | 8/2009 | Cooke | G01N 1/2273 422/562 |
| 9,097,624 | B1* | 8/2015 | Bottiger | A47L 7/0085 |
| 2007/0137319 | A1* | 6/2007 | Nacson | G01N 1/02 73/864 |
| 2008/0127949 | A1* | 6/2008 | Herald | F02M 35/024 123/519 |
| 2008/0184515 | A1* | 8/2008 | Chapman | A47L 9/02 15/246.2 |
| 2012/0152038 | A1* | 6/2012 | Cho | G01N 1/2205 73/863.12 |
| 2013/0255403 | A1* | 10/2013 | Dixon | G01N 1/08 73/863.23 |
| 2014/0245843 | A1* | 9/2014 | Bry | G01N 1/2211 73/864.63 |

FOREIGN PATENT DOCUMENTS

| WO | 2006093517 | 9/2006 |
|---|---|---|
| WO | 2009061863 | 5/2009 |

\* cited by examiner

SAMPLING DEVICE

FIELD OF THE INVENTION

The present invention is in the field of devices for collecting substance traces or residues for chemical testing and more specifically in the field of sampling devices for detection of explosives/narcotics traces, gunshot residues, or of any other substance of interest traces.

BACKGROUND OF THE INVENTION

Due to international terrorism and other crime related threats, law enforcement and homeland security forces are always in seek for improved detection methods and devices which will allow them to more securely and effectively cope with such threats. Improvements in the existing devices and methods, as well as the provision of new devices and methods, are generally directed towards one or more of the following benefits: reducing the costs involved in equipping law enforcement manpower with appropriate detection devices, increasing the reliability of detection, reducing the time to be invested in a checking event, reducing the level of expertise required for carrying out the checking procedure and making it more comfortable for decent persons who may undergo screening procedures due to strict security demands.

The devices currently available for detection of trace explosives/narcotics and gunshot residues are of one of the two following main categories: (i) devices called sniffers, which are vapor detection devices, specializing in automated analysis of trace explosives/narcotics in the form of vapors. Such vapors may be present in the atmosphere of a detected region before being collected into a computerized analyzing unit by suction (i.e. collection by a vacuum or vacuum vortex system), or may be prepared for the analysis from sampled particles by heating them for evaporation thus allowing delivery of the vapors released from the particles into the computerized analyzing unit by suction; and (ii) chemical kit devices for particles detection, for identification of potential threats according to color changes in chemical reactions visually identifiable by a user when a particle of interest, drug or explosive, reacts with preprepared chemical reagents provided as part of the kit.

Generally, vapor detection methods are orders of magnitudes more sensitive comparing to visual detection of color changes in chemical reactions (nanograms to picograms detection sensitivity in vapor detection methods comparing to micrograms to nanograms detection, sensitivity in color chemically based detection methods, depending on the particular substance examined). Such extraordinary sensitivity of vapor detection methods may be considered advantageous in some aspects, however several drawbacks may be associated with the vapor detection approach:

i. The technologies underlying vapor detection are highly expensive. Mobile device such as QS-H150™ or Sabre 5000™ of Smithdetection™ are priced in the range of tens of thousands US dollars, thus are financially affordable only for special check spots, such as air ports and border terminals, while small terminals, police patrol vehicles and the like are equipped with chemical test kits.

ii. The extremely high sensitivity of vapor detection devices exposes them to operation interruptions due to possible self contamination. It is expected that even a small particle of illicit drugs or explosives which incidentally may happen to cross the filtering system of the device will cause it to maintain either a constant or an unexpectedly repeating false positive alarm due to the vapors released from the particle. It can take some hours for a trained person to dismantle the device, clean it and return it to normal operation.

iii. Low vapor pressure explosives like PETN or RDX have equilibrium vapor concentration in air of as low as near one part per trillion (1 ppt) level, which \ vapor detection are incapable of effectively recognize detection iv. About 1% of false positive detection is expected in normal operation of vapor detection devices, according to manufacturer's specifications.

In view of these, when screening events are occasional, random, or in moderate numbers, particle detection by color change of a chemical reaction is advantageous in terms of both price and reliability, when referring to trace explosives/narcotics detection directed to suspected people, cars, baggage and the like. Particles detection is disadvantageous however in terms of sample collection efficiency.

The main problems associated with sample collection of trace particles of explosives and narcotics are discussed in the background chapter of U.S. Pat. No. 7,574,930. This document also distinguishes between a contact sample collection procedure in which sample is collected from the suspected object by wiping, and between a non-contact particles collection procedure in which a sample is collected by vacuum or by vacuum vortex based collecting means. It is understood from the background of said patent that due to possible strong surface adhesion forces of explosives and narcotics, the power of the air flow applied to a target surface by vacuum and vacuum vortex collection methods is insufficient to remove particles of explosives and narcotics from rigid surfaces, unless the collection method is successfully improved as suggested in the specification of said U.S. patent.

It can be appreciated accordingly, that the most reliable method for particles collection of explosives and narcotics is by wiping. Disadvantageously, however, sampling by wiping is (i) time consuming when applied to large surface areas, and (ii) is considered uncomfortable and invasive when applied to a person's body and clothing.

Successful application of the improvements of the sampling device suggested by U.S. Pat. No. 7,574,930 may improve the efficiency of particle sampling for chemically based color test, with the price of reducing the reliability of a test due to potential contamination of a current test by traces of substances of interest acquired by the suction device in previous tests. While computerized sniffers may comply with this problem by self calibration of the device as a preparation step to be taken before every new sampling, chemically based test kits for color change detection are unable to distinguish between a particle of interest acquired during a current sampling event and between contamination of the current test by previously acquired traces of materials. The device suggested by U.S. Pat. No. 7,574,930 is thus not sufficiently reliable for chemical tests.

Chemically based detection is thus commonly based on suspected particles collection by wiping, e.g. as suggested by the following patents.

A chemical kit device for particle detection by wiping is disclosed by WO2006093517 titled spot test kit for explosives detection. The kit device comprises a body, a lateral flow membrane swab unit adapted to be removably connected to the body, two explosives detecting chemical reagents, two chemical reagent holders and dispensers operatively connected to the body, the two chemical reagent holders and dispensers are respectively containing the two explosives detecting chemical reagents and are positioned to deliver the explosives chemical reagents to the lateral flow membrane swab unit when the lateral flow membrane swab unit is connected to the body. The swab unit has a sample pad to be exposed to a suspect substance when the sample pad is swiped across a surface containing the suspect substance or in other ways such as adding the suspicious substance to the sample pad.

U.S. Pat. No. 7,410,612 relates to a gunpowder particle test kit for determining gunpowder traces, which includes a transparent sleeve having a closed end and an open folded end sealed with a clip forming a sealed cavity carrying a test strip and a crushable ampoule carrying a diphenylamine solution. The test strip has an adhesive area on a front surface. An opaque label is provided on a rear surface on the sleeve opposite the adhesive area. In use, the clip is removed to open the cavity, the test strip removed and applied by wiping to possible traces areas on a subject. The strip is returned to the cavity; the clip reapplied to seal the cavity. Thereafter, the ampoule is crushed to release the solution, which develops a distinctive coloration observable against the label to indicate the presence of possible gunpowder traces.

It is thus within the aims of the present invention to improve the collection method for chemically based detection of explosives/narcotics traces and gunshot residues, simplifying the preparation of a trace sampling device that will collect efficiently suspected particles and will eliminate false positives due to contamination acquired during previous tests.

SUMMARY OF THE INVENTION

In a first broad aspect, the invention relates to a particles collecting and detecting system for analysis in the level of particles as are (i.e. without evaporating the collected particles) the system comprising (i) a vacuum generating unit having an air intake opening, (ii) a particles collecting unit having a body, a duct extending through the body and connecting between a rear opening of the body and an air intake opening of the body, and an aperture or slit in a mid portion of the body adapted for receiving a removable sampling member into a position within the duct; (iii) a disposable sampling probe having a sampling member adapted to be removably inserted into a position within the duct through said aperture or slit, for being exposed to air flow forced by the vacuum generator from the air intake orifice to the air intake opening during a single sample collection event, and (iv) a test kit (preferably adapted for receiving and holding the sampling member after its removal from the duct), adapted for exposing the sampling member to chemical reagents and for visualizing a color change in response to a reaction between the chemical reagents and a particles of interest trapped by the sampling member during its exposure to the air flow within the duct. In a preferred embodiment of the system, the particles collecting unit is disposable, i.e. configured for fast replacement by a similar new unit before every new screening test, by being detachably couple-able to the vacuum generating unit, preferably by user hands without requiring the aid of tools. In various preferred embodiments the sampling member is impermeable to air flow. In special check points where budget allows or were circumstances oblige, a special equipment for analyzing substances in the particle level (without evaporation), e.g. SEM (Scanning Electronic Microscope) can be used in addition to the disposable test kit for recognizing the nature of a sample screened by the particles collecting unit. Such special equipment will preferably have holding means matching the sampling probe, so as to locate the sampling member in position within the special equipment.

The duct in the body of the particles collecting unit may have a converging contour from the air intake orifice to just in front of the position of the sampling member. Whether or not the duct is of a converging contour, the duct is preferably designed such that a front surface of the sampling member is dimensioned to face next to it (i.e. a few millimeters towards the air intake orifice) a smaller dimensioned cross section area of the duct. The duct then continues with lateral widening about circumferential edges of the sampling member. Another portion of the duct joins between said widening and the rear opening of the body, leaving an air gap between circumferential edges of the sampling member and between walls of the duct. The sampling member's front has thus a surface area facing the air intake orifice similar and preferably greater than a cross section area of the duct just before said widening, such that particles swept by the air flow gain momentum sufficient to prevent them from escaping a collision with the front of the sampling member, while most air molecules do escape such collision by moving through the air gap formed between the circumferential edges of the sampling member and between the walls of the duct near said lateral widening.

In preferred embodiments of the invention the front of the sampling member is provided with adhesive coating sealed by a disposable protective piece to be disposed for uncovering the adhesive before inserting the sampling member through the aperture or slit into position within the duct. Preferably said adhesive coating is provided as a double sided sticker (e.g. trimmed from a double sided adhesive mounting tape), a back side of which being permanently attached to the front of the sampling member and a front side of which being protected by said disposable protective piece (adhesive tape liner). In various preferred embodiments of the invention the double sided sticker is formed of a spongy material between 0.25 to 1 mm thick. In yet further preferred embodiments high adhesive coating weight is provided as the front of the sampling member for improving particle trapping.

In a successful sampling experiment carried out by the inventors the carrier of the adhesive mounting tape was of a PVC film, which was coated by modified acrylic adhesive protected by a siliconized paper as a liner. The thickness of the tape (without liner) was 0.28 mm.

In a second broad aspect the invention relates to a particles collecting unit allowing for identifying substances by analyzing particles in the level of particles as are (i.e. without evaporating the collected particles), the unit comprises a body, a duct extending through the body and connecting between a rear opening of the body and an air intake orifice of the body, and an aperture or slit in a mid portion of the body adapted for receiving a removable sampling member into a position within the duct, wherein the particles collecting unit is configured to be removably coupled to a vacuum generator with said rear opening of the body coupled to an air intake opening of the vacuum generator.

Preferably, the particles collecting unit is provided within a clean envelope for being disposably used, one unit per a screening test.

Replacing both the sampling probe and the particle collecting unit body before each new test prevents the possibility of cross contamination between successive screening events and highly increases the reliability of the detection procedure as a legal evidence for the presence of traces of a substance of interest, once detected.

In preferred embodiments of the invention the design of the body of the particles collecting unit is configured to match the design of a body having the air intake opening of a domestic portable battery operated vacuum cleaner of a type available in the free market, such that the two matching bodies can be secured together, with the rear opening in the body of the particles collecting unit coupled to the air intake opening of the vacuum cleaner. For example, the particles collecting unit illustrated in FIGS. 1 and 2 of the present invention is configured to match the air intake opening of conventional Dyson™ portable vacuum cleaner such as DC31 model. The particle collecting unit is further provided with pressure release openings at it walls for reducing the load on the motor of the vacuum cleaner and for adapting its suction power for sample collecting tasks. For best results, the size of the openings in the walls of a particles collecting unit intended for use with a specific vacuum generating unit can be determined and optimized experimentally by using prototype models of the particles collecting unit differing in the size and/or number and/or locations of pressure release openings, before turning to a mass production of a unit with a desired number size and location of openings.

Indentation is provided in the edge of the air intake orifice of the sample collecting unit to prevent removal of particles of interest from the examined surface when the edge of the orifice is moved over the surface during contact collection. The indentation is useful as well for reducing adherence by suction of examined fabrics, e.g. of clothing of a detected person, to the air intake orifice. Furthermore, the indentation improves air flow from the surrounding atmosphere into the air intake orifice thereby improving sweeping of particles from the examined surface into the duct.

In some embodiments of the invention, the body of the sample collecting unit may comprise near the air intake orifice means such as bristles, for improving and facilitating release of particles of explosives or narcotics from examined surfaces for being swept by the air flow into the intake orifice.

The particles collecting unit is removable and couple-able to the vacuum generating unit with the rear opening coupled to the air intake opening such that when the vacuum generating unit operates with the sample collecting unit coupled to it, air flow is forced from the vicinity of the air intake orifice of the particles collecting unit through the duct passed the sampling member and into the air intake opening of the vacuum generator. The body further comprises a through aperture or slit in a mid portion thereof and walls of the aperture or slit constitute and/or cooperate with guiding and holding members for a sampling probe. The sampling probe is contoured to match the guiding and holding members such that a particles collecting member of the sampling probe can be inserted through said aperture or slit and be brought to a predetermined position within the duct in which it is being held by said holding members, and such that particles swept by the air flow passing through the duct hit the sampling member.

In a third broad aspect the invention relates to a sampling probe comprising a gripping member and a sampling member wherein the sampling member is dimensioned and oriented about the gripping member to face (i) an air intake orifice of a particles collecting unit once inserted into position within a duct extending along the body of the particles collecting unit; and (ii) a transparent inspection window of a reaction chamber of a chemical test kit, once removed from the particles collecting unit and inserted into a position within the chemical test kit.

In various preferred embodiments of the invention the sampling member is impermeable to air molecules, and the test kit and the sampling probe are of a type similar to the molded casing exemplified in FIGS. 2a to 6 of U.S. Pat. No. 7,829,019, wherein the tip portions of the probe (numbered 52 and 53 in FIG. 3a of U.S. Pat. No. 7,829,019) are substituted by a sampling member having a substantially flat region to be facing both (one at a time) (i) the air intake orifice of the particles collecting member, and (ii) the inspection window of the reaction chamber; wherein said flat region is coated by adhesive material protected by a removable liner to be peeled off before screening a suspected object.

In a fourth broad aspect the invention relates to a sampling and detection method of explosives, narcotics traces and gunshot residues. The method includes contact collection of suspected particles, yet is significantly more comfortable and in the same time more effective and reliable in comparison with methods that include sample collection by wiping. The method comprises providing a particles collecting unit (disposable according to the preferred embodiment of the method), a disposable sampling probe, and a chemical test kit for detecting either explosives, narcotics traces or gunshot residues or of any other substance of interest according to a color change of a reaction between particles of a substance of interest and reagents provided in the test kit, wherein the particles collecting unit, the sampling probe and a casing of the test kit are mutually contoured and dimensioned such that the sampling member can be inserted into a predetermined position within a duct of the particles collecting unit for facing an air intake orifice for trapping particles of interest, and then removed from the particles collecting unit and inserted into a predetermined position within the reaction chamber of the test kit facing the inspection window.

Preferably, the particles collecting unit, the sampling probe and the chemical test kit are disposable, and the method comprises the step of replacing all said three parts by similar new ones per each new screening.

DETAILED DESCRIPTION OF THE FIGURES

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

Figure 1:
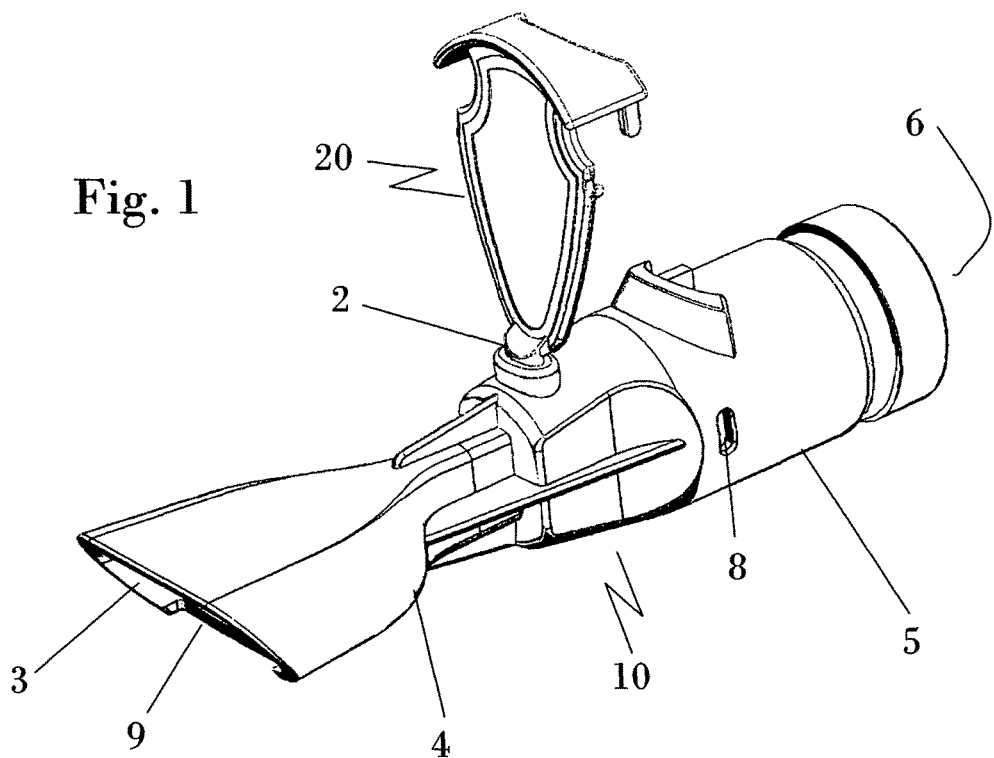
FIG. 1 illustrates a disposable particles collecting unit according to the invention, in a perspective view.

FIG. 1 illustrates a disposable particles collecting unit (1) according to the invention, in a perspective view, with a sampling probe (20) in its operative sample collecting position.

Figure 2:
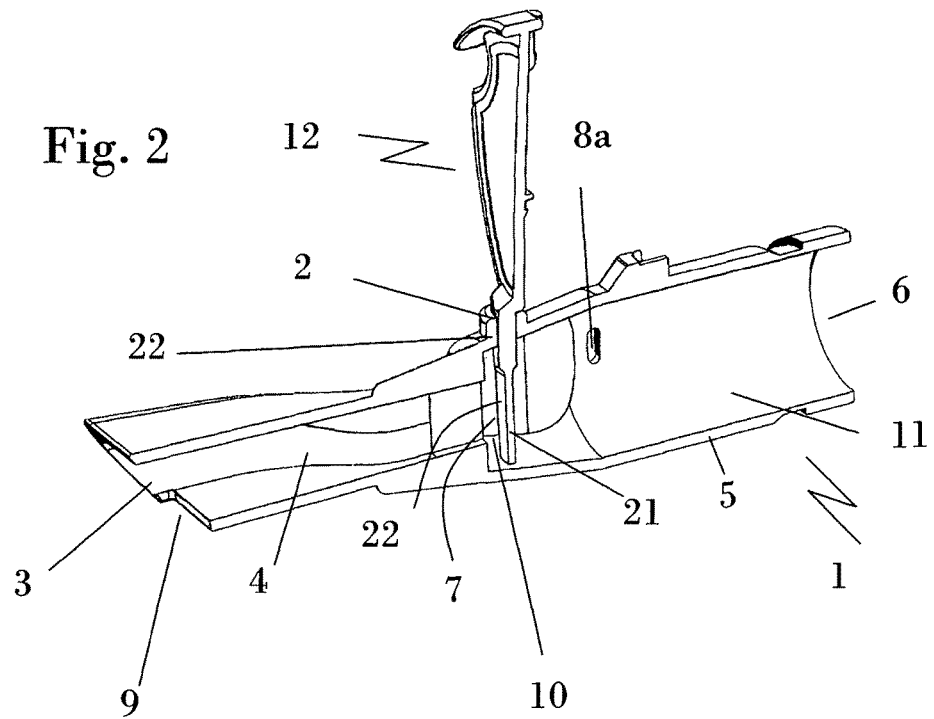
FIG. 2 illustrates a longitudinal cross sectional perspective of the particles collecting unit illustrated in FIG. 1.

FIG. 2 illustrates a longitudinal cross sectional perspective of the particles collecting unit (1) illustrated in FIG. 1.

The following description refers to both said FIGS.

The particles collecting unit comprises a body (1), a duct ((11) of FIG. 2) extending through the body and connecting between a rear opening (6) of the body (1) and an air intake orifice (3) of the body (1), and an aperture or slit (2) in a mid portion of the body (1) adapted for receiving a removable sampling member (21) (hidden within the body in the FIG. 1, but shown in FIG. 2) into a position within the duct (4), wherein the particles collecting unit is configured to be removably coupled to a vacuum generator (not shown) with said rear opening (6) of the body (1) coupled to an air intake opening of the vacuum generator. In the depicted embodiment, the particles collecting unit is of a type configured to match the air intake opening of conventional Dyson™ DC31 model portable vacuum cleaner. The particle collecting unit is further provided with pressure release openings ((8) shown in FIG. 1 and (8a) shown in FIG. 2) at it walls for reducing the load on the motor of the vacuum cleaner and for adapting its suction power for sample collecting tasks. The particles collecting unit is removably couple-able to a vacuum generating unit (the depicted unit is designed for coupling to a domestic Dyson™ DC31 vacuum cleaner, but as a matter of preference one can design the particles collecting unit so as to match any other preferred vacuum cleaner/generator) with the rear opening (6) coupled to the air intake opening of the vacuum generating unit such both units become secured together and such that when the vacuum generating unit operates with the sample collecting unit (1) coupled to it, air flow is forced from the vicinity of the air intake orifice (3) of the particles collecting unit (1) through the duct (11) passed the sampling member (21) and the rear opening (6) and into the air intake opening of the vacuum generator.

Indentation (9) is provided in the edge of the air intake orifice (3) of the sample collecting unit (1) to prevent removal of particles of interest from the examined surface (not illustrated) when the edge of the orifice (3) is moved over the surface during contact collection. The indentation (9) is useful as well for reducing adherence by suction of examined fabrics, e.g. of clothing of a detected person, to the air intake orifice (3). Furthermore, the indentation (9) improves air flow from the surrounding atmosphere into the air intake orifice (3) thereby improving sweeping of particles from the examined surface into the duct (11).

The through aperture or slit (2) in the mid portion of the body (1) has surrounding walls (12) which constitute guiding and holding members for the sampling probe (20). The sampling probe (20) is contoured to match the guiding and holding members (12) such that the particles collecting member (21) (see FIG. 2) of the sampling probe (20) can be inserted through said aperture or slit (2) and be brought to a predetermined position within the duct (11) in which it is being held by said holding members (12), such that particles swept by the air flow passing through the duct hit the sampling member (21). The duct (11) in the body of the particles collecting unit (1) have a converging contour (4) from the air intake orifice (3) to just in front of the position of the sampling member (21). In this preferred embodiment the duct (11) is designed such that a front surface (22) of the sampling member (21) is dimensioned to face a few millimeters next to it (i.e. a few millimeters towards the air intake orifice (3)) a smaller dimensioned cross section area (4a) of the duct. The duct then continues by with lateral widening (10) about circumferential edges of the sampling member (21). Another portion of the duct joins between said widening (10) and the rear opening (6) of the body (1), leaving an air gap (7) between circumferential edges of the sampling member (21) and between walls of the duct. The sampling member's front has thus a surface area (22) facing the air intake orifice (3) similar and slightly greater than a cross section area (4a) of the duct just before said widening (10), such that particles swept by the air flow gain momentum sufficient to prevent them from escaping a collision with the front (22) of the sampling member (21), while most air molecules do escape such collision by moving through the air gap (7) formed between the circumferential edges of the sampling member (21) and between the walls of the duct near said lateral widening (10). The front of the sampling member (21) is provided with adhesive coating (22). Before use, the adhesive coating is sealed by a disposable protective piece (not shown) to be disposed for uncovering the adhesive before inserting the sampling member (21) through the aperture or slit (2) into position within the duct (11). Preferably said adhesive coating is provided as a double sided sticker (e.g. trimmed from a double sided adhesive mounting tape), a back side of which being permanently attached to the front of the sampling member and a front side of which being protected by said disposable protective piece (adhesive tape liner). In various preferred embodiments of the invention the double sided sticker is formed of a spongy material between 0.25 to 1 mm thick. In yet further preferred embodiments high adhesive coating weight is provided as the front of the sampling member for improving particle trapping. In a successful sampling experiment carried out by the inventors the carrier of the adhesive mounting tape was of a PVC film, which was coated by modified acrylic adhesive protected by a siliconized paper as a liner. The thickness of the tape (without liner) was 0.28 mm.

The sampling member (21) in the depicted preferred embodiment is impermeable to air molecules, and the sampling probe (22) as a whole (except for the sampling member (21)) is of a design similar to the design of the sampling probe of the molded casing exemplified in FIGS. 2a to 6 of U.S. Pat. No. 7,829,019, wherein the tip portions of the probe (numbered 52 and 53 in FIG. 3a of U.S. Pat. No. 7,829,019) are substituted by the sampling member (21) of the present invention, which has a substantially flat region (22) to be facing both (one at a time) (i) the air intake orifice (3) of the particles collecting unit (1), and (ii) the inspection window of the reaction chamber numbered 29 in FIG. 4b of U.S. Pat. No. 7,829,019, wherein said flat region (22) is coated by adhesive material which is protected by a removable liner to be peeled off before screening a suspected object.

Figures 3A, 3B:
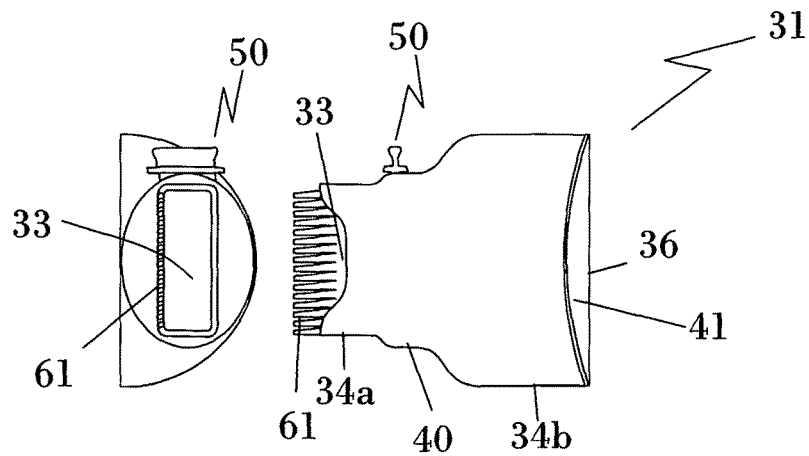
FIG. 3A illustrates a top view of another embodiment of a particles collecting unit according to the invention.
FIG. 3B illustrates a front view of the particles collecting unit illustrated in FIG. 3A.
Figures 3C, 3D, 3E, 3F:
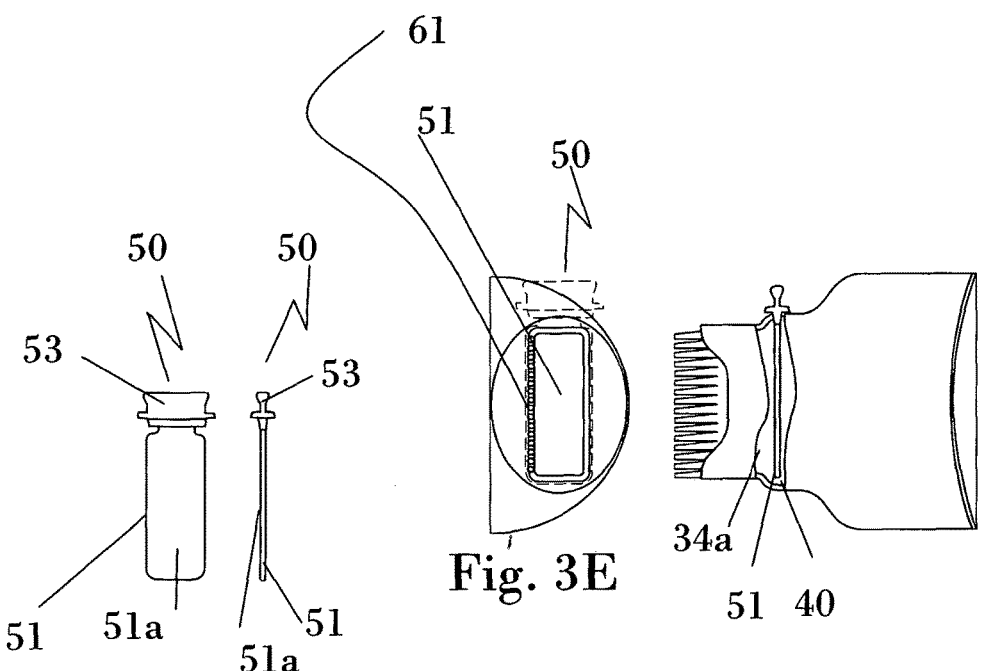
FIG. 3C illustrates a face view of the sampling probe of the particles collecting unit illustrated by FIGS. 3A &3B.
FIG. 3D illustrate a side view of the sampling probe illustrated in FIG. 3C.
FIG. 3E illustrates the front view of the particles collecting unit illustrated in FIG. 3B while using a dotted line for exemplifying that the sampling member has a surface area greater than the area of the duct in front of it.
FIG. 3F illustrates the particles collecting unit illustrated by FIG. 3A, with a partial section in the body of the unit for viewing the sampling member in position inside the unit's body.

FIG. 3A illustrates a top view of another embodiment of a particles collecting unit according to the invention. The particle collecting unit (31) may be especially useful for dress/clothing/fabrics screening tasks and comprises a body having a rear opening (36), an air intake orifice (33) and a duct (41) communicating between said openings through the body of the unit (31). A sampling probe (50) is shown in its operative position, prepared for a sampling task. A sampling member (51) of the sampling probe (50) can be seen in FIG. 3B through the air intake orifice (33), with a front surface of the sampling member (51) facing the orifice (33). The sampling member (51) is connected to a gripping member (53) of the sampling probe (50). The sampling member (51) is removably inserted into the body of the sample collecting unit (31) through an insertion slit/aperture (32) formed in a mid portion (40) in the body of the sample collecting unit (31). The sampling probe (50) is designed to snugly fit into the slit/aperture (32) such that the position of the sampling member (51) within the duct (41) is properly kept during the sampling procedure. The proper position of the sampling member (51) within the duct is shown in FIG. 3F through a partial cut formed for descriptive purpose in the wall of the unit (31). The body of the particle collecting unit (31) is narrower in its front region (34) than in its region (40) where the sampling member (51) is positioned, thus allowing the front surface area of the sampling member (51) to be greater than the cross sectional area of the duct (41) in the front region (34), with a gap (40) (see FIG. 3F) still formed between the circumferential edges of sampling member (51) and the body of the particle collecting unit (31). In FIG. 3E the sampling probe (50) is illustrated by a dotted line, thus exemplifying that the sampling member (51) has a surface area greater than the area of the duct in front of it. A rear region (34*b*) of the body of the particle collecting unit (31), is formed wider than the remaining of the body so as to allow coupling the particle collecting unit (31) to an air intake of a domestic vacuum cleaner (not illustrated) having a matching design and constituting a vacuum generator, with the rear opening (36) of the particle collecting unit (31) coupled and secured to the air intake of the vacuum cleaner. Once secured together and the vacuum generating unit operates with the sample collecting unit (31) coupled to it, air flow is forced from the vicinity of the air intake orifice (33) of the particles collecting unit (31) through the duct (41) passed the sampling member (51) and the rear opening (36) and into the air intake opening of the vacuum generator.

In the present embodiment, the end of the body of the sample collecting unit near the air intake orifice (33) is provided with bristles (61), for improving and facilitating release of particles of explosives or narcotics from examined uneven surfaces (e.g. clothing and fabrics) for being swept by the air flow into the intake orifice (33). The bristles (61) can be produced in the molding process of the plastic body of the sample collecting unit (31) from the same molded plastic, and alternatively can be formed from any acceptable material and integrated to the body of the unit (31) using any desired connecting method. Indentation (39) is preferably provided in the edge of the unit's wall next to the wall where the bristles (51) are, to prevent removal of particles of interest from the examined surface (not illustrated) when the edge of the orifice (33) is moved over the surface during contact collection of a sample.

FIG. 3C illustrates a face view of the sampling probe (50) of the particles collecting unit (31) illustrated by FIGS. 3A &3B. FIG. 3D illustrate a side view of the sampling probe illustrated in FIG. 3C. The sampling member (51) of the sampling probe (50) is covered with adhesive material, such that when sampled particles are swept into the air intake orifice (33) by air flow generated by the vacuum generator, they hit the face of the sampling member (51) facing the intake orifice (33), and are caught by the adhesive material for later examination through a chemical test. The adhesive coating will always correctly face the air intake orifice (33) by designing the sampling probe so as not to fit into place case of unintentionally trying to insert the sampling probe into the unit through the insertion slit/aperture with the adhesive coating facing to the wrong direction.

The invention claimed is:

1. Particle collecting unit for collecting particles in the particle level of substance without evaporating the collected particles, comprising a body, a duct extending through the body and connecting between a rear opening of the body and an air intake orifice of the body, and an aperture or slit in a mid portion of the body adapted for removably receiving a sampling member into a position within the duct, wherein the particles collecting unit is configured to be removably coupled to a vacuum generator of a vacuum cleaner with said rear opening of the body coupled to an air intake opening of the vacuum generator, and wherein walls of the duct comprise openings configured for reducing the load on a motor of a vacuum cleaner when the particle collecting unit is coupled to an operating vacuum cleaner with said sampling member in position within the duct, and wherein said openings for reducing the load on the motor are located on wall portions of the duct remoter from the air intake orifice than a location of the sampling member when in position within the duct.

2. Particle collecting unit according to claim 1, further comprising a sealed disposable envelope wrapping the particle collecting unit, whereby the particle collecting unit can be maintained clean until being used per a screening test.

3. Particle collecting unit according to claim 1, configured to match the air intake opening of a portable vacuum cleaner of a model available in the market.

4. Particle collecting unit according to claim 1, wherein the pressure release openings are provided in a mid-portion of the duct such that they are closer to the rear opening of the body than the sampler receiving aperture or slit.

5. Particle collecting unit according to claim 1, wherein indentation is provided in the edge of the air intake orifice of the sample collecting unit.

6. Particle collecting unit according to claim 1, further comprising a sampling probe, the sampling probe comprising a gripping member and a sampling member, wherein the sampling member is dimensioned and oriented about the gripping member to face (i) an air intake orifice of a particles collecting unit once inserted into position within a duct extending along the body of the particles collecting unit; and (ii) a transparent inspection window of a reaction chamber of a predetermined chemical test kit mutually contoured and dimensioned to receive the sampling probe, once the sampling probe being removed from the particles collecting unit and inserted into a position within the predetermined chemical test kit.

7. Particle collecting unit according to claim 1, in combination with particles collecting and detecting system, the system comprising the particles collecting unit, further comprising (i) a vacuum generating unit having an air intake opening adapted for coupling with the rear opening of the particles collecting unit; (ii) a disposable sampling probe having a sampling member adapted to be removably inserted into a position within the duct of the particles collecting unit through the aperture or slit in the body of the particles collecting unit, for being exposed to air flow forced by the vacuum generator from the air intake orifice to the air intake opening during a single sample collection event, and (iii) a test kit adapted for exposing the sampling member to chemical reagents and for visualizing a color change in response to a reaction between the chemical reagents and particles of interest trapped by the sampling member during its exposure to the air flow within the duct.

8. Particle collecting unit according to claim 7, wherein the test kit is adapted for receiving and holding the sampling member in a predetermined position.

9. Particle collecting unit according to claim 1, wherein the duct has a converging contour from the air intake orifice to just in front of the position of the sampling member.

10. Particle collecting unit according to claim 7, wherein the duct and the sampling member are mutually designed such that when in position within the duct, an area of a front surface of the sampling member facing the intake orifice is smaller then a cross section area of the duct immediately next to said front surface in a direction toward the intake orifice, and is greater than a cross section area of a duct portion further in direction toward the intake orifice.

11. Particles collecting and detecting system according to claim 7, wherein an air gap is left between circumferential edges of the sampling member and between walls of the duct.

12. Particles collecting and detecting system according to claim 7, wherein a face of the sampling member is provided with adhesive coating.

13. Particles collecting and detecting system according to claim 12, wherein the adhesive coating is sealed by a disposable protective piece to be disposed for uncovering the adhesive before inserting the sampling member into position within the duct.

14. Particles collecting and detecting system according to claim 12 wherein the adhesive coating is provided as a double sided sticker formed of a spongy material between 0.25 to 1 mm thick.

15. Particles collecting and detecting system according to claim 12, wherein the adhesive coating is provided as a high weight coating at least 0.25 mm thick.

16. Method for chemically based detection of suspected particles, the method comprising (i) providing a particles collecting unit for collecting particles in the particle level of substance without evaporating the collected particles, comprising a body, a duct extending through the body and connecting between a rear opening of the body and an air intake orifice of the body, and an aperture or slit in a mid-portion of the body adapted for removably receiving a sampling member into a position within the duct, wherein the particles collecting unit is configured to be removably coupled to a vacuum generator of a vacuum cleaner with said rear opening of the body coupled to an air intake opening of the vacuum generator, and wherein walls of the duct comprise openings configured for reducing the load on a motor of a vacuum cleaner when the particle collecting unit is coupled to an operating vacuum cleaner with said sampling member in position within the duct, and wherein said openings for reducing the load on the motor are located on wall portions of the duct remoter from the air intake orifice than a location of the sampling member when in position within the duct; (ii) providing a disposable sampling probe comprising a sampling member and a gripping member; (iii) providing a chemical test kit for detecting either explosives, narcotics traces or gunshot residues or of any other substance of interest, according to a color change of a reaction between particles of a substance of interest and reagents provided in a casing of the test kit; wherein the particles collecting unit, the sampling probe and the casing of the test kit are mutually contoured and dimensioned to allow the sampling member of the sampling probe to be removably inserted either into a predetermined position within the duct of the particles collecting unit for facing an air intake orifice thereof for trapping particles of interest, or into a predetermined position within a reaction chamber formed in the casing of the test kit facing an inspection window thereof, wherein the gripping member extends from the sampling member to allow it protrude out of a wall of the particles collecting unit when the sampling member is in position within the particle collecting unit; the method further comprising (iv) connecting the particle collecting unit to a vacuum generator with a rear opening of the body of the particle collecting unit coupled to an air intake opening of the vacuum generator; (v) placing the sampling member in a predetermined position within the particle collecting unit; (vi) activating the vacuum generator thereby generating air flow into an air intake orifice of the particle collecting unit such that particles of interest can be swept by the airflow and collected by the sampling member; (vii) removing the sampling probe from the particle collecting unit and inserting it into a predetermined position within the reaction chamber of the chemical test kit in front of the inspection window, for chemically detecting the collected particles.

17. The method according to claim 16, further comprising the step of replacing all three parts (a) particle collecting unit, (b) sampling probe, and (c) test kit, per each new screening.

18. Particle collecting unit for collecting particles in the particle level of substance without evaporating the collected particles, comprising a body, a duct extending through the body and connecting between a rear opening of the body and an air intake orifice of the body, and an aperture or slit in a mid-portion of the body adapted for removably receiving a sampling member into a position within the duct, wherein the particles collecting unit is configured to be removably coupled to a vacuum generator of a vacuum cleaner with said rear opening of the body coupled to an air intake opening of the vacuum generator, and wherein walls of the duct comprise openings configured for reducing the load on a motor of a vacuum cleaner when the particle collecting unit is coupled to an operating vacuum cleaner with said sampling member in position within the duct, and wherein the openings for reducing the load on the motor are arranged symmetrically with respect to the sampling member when in position within the duct.

* * * * *